United States Patent [19]

Kapp et al.

[11] Patent Number: 5,015,475
[45] Date of Patent: May 14, 1991

[54] METHOD AND MEANS FOR PREVENTING OR DELAYING UNDESIRED PHOSPHINE LEVELS

[75] Inventors: Wolfgang Kapp; Alfons Moog, both of Laudenbach, Fed. Rep. of Germany

[73] Assignee: Degesch GmbH, Laudenbach, Fed. Rep. of Germany

[21] Appl. No.: 351,137

[22] Filed: May 12, 1989

[30] Foreign Application Priority Data

May 14, 1988 [GB] United Kingdom ............... 8811476
May 14, 1988 [GB] United Kingdom ............... 8811477

[51] Int. Cl.$^5$ ............................................. A61K 9/14
[52] U.S. Cl. ................................ 424/405; 424/40; 424/409
[58] Field of Search ............... 424/601, 405, 409, 40; 43/137.1

[56] References Cited

U.S. PATENT DOCUMENTS

| | | | |
|---|---|---|---|
| 3,132,067 | 5/1964 | Rauscher et al. | 424/405 |
| 3,719,751 | 3/1973 | Rauscher et al. | 424/601 |
| 4,013,790 | 3/1977 | Kapp | 424/601 |
| 4,200,657 | 4/1980 | Cook | 422/40 |
| 4,210,683 | 7/1980 | Praxl et al. | 424/601 |
| 4,490,352 | 12/1984 | Miller | 424/601 |
| 4,592,855 | 6/1986 | Gioffre et al. | 424/40 X |
| 4,761,395 | 8/1988 | Tom et al. | 521/28 |
| 4,889,708 | 12/1989 | Latif et al. | 424/601 |
| 4,894,230 | 1/1990 | Friemel et al. | 424/405 |

FOREIGN PATENT DOCUMENTS 1589 5/1979 European Pat. Off.
56-045401 4/1981 Japan.
56-053603 5/1981 Japan.
61-53106 3/1986 Japan.
61-152603 7/1986 Japan.
61-215301 9/1986 Japan.

OTHER PUBLICATIONS

CA82:103609c, Adsorptive power of some adsorbents as regards to phosphine, Tkach (1975).

Primary Examiner—Thurman Page
Assistant Examiner—R. Harrison
Attorney, Agent, or Firm—Millen, White & Zelano

[57] ABSTRACT

The invention serves to prevent or delay the formation of undesired phosphine levels in packages in which phosphine releasing compositions (in particular hydrolysable metal phosphides) are packaged and stored and in environments to be fumigated during the period of introduction of phosphine-releasing compositions. This is brought about by maintaining in the immediate vicinity of the composition a zeolite having a pore width from 0.3 nm upwards, preferably 0.4 to 1.5 nm and an adsorbtive affinity for moisture or phosphine or preferably both. The zeolite is employed either as a separate item in the package or as part of the composition, admixed or as a coating. In a mass ratio of metal phosphide to zeolite are from 1:0.05 to 1:2. The adsorption of phosphine to the zeolite is reversible and on exposure to an environment to be subjected to pest control, the zeolite will release the adsorbed phosphine by replacement by atmospheric humidity. The zeolite loaded with phosphine is itself useful as a pest control agent.

27 Claims, 1 Drawing Sheet

METHOD AND MEANS FOR PREVENTING OR DELAYING UNDESIRED PHOSPHINE LEVELS

BACKGROUND OF THE INVENTION AND PRIOR ART

The invention relates to a method of and means for preventing or delaying the formation of undesired phosphine levels in a space or environment, the phosphine being derived from phosphine liberating compositions, in particular comprising hydrolysable metal phosphides, by delaying the onset of phosphine generation and/or by removal of phosphine already generated.

Pest control agents in solid form are known which when exposed to air slowly evolve gaseous components including phosphine. Such pest control agents are, for example adapted to generate hydrogen phosphide from hydrolysable alkaline earth and/or earth metal phosphides, in particular from aluminium phosphide, calcium phosphide and magnesium phosphide, when acted upon by the moisture content of air or stored commodities. Such pest control agents are employed for example for combating pests such as beetles, bugs, worms, cockroaches or other insects and their eggs and larvae but also rodents, e.g. mice and rats, e.g. in stores, mills, shipholds, railway carriages, trucks, containers, storage sheds, plastic lined earth silos and dumps in sheds or under canvas or permanent silos for grain, legumes, nuts, cocoa beans, tobacco or other foodstuffs or luxury goods, animal feeds and other processed or unprocessed commodities and various environments whether used for storage or containing such commodities or not.

Such phosphine releasing pest control agents have in the past 10 to 20 years gained the upper hand to an increasing extent over other fumigating agents such as methyl bromide, ethylene dibromide and ethylene oxide. Reasons for this are on the one hand the favourable properties of hydrogen phosphide; it in no way impairs the quality of most fumigated commodities, rapidly penetrates into the interior, e.g. in the case of grain into the seeds, and there destroys animal organisms including all their development stages. Yet after the fumigation has been completed, the phosphine is dissipated just as rapidly again by aeration. On the other hand the application is relatively simple because the products, e.g. in the form of pressed bodies such as tablets and pellets can either be admixed to the flow of grain or be spread out on the floor of storage halls. However, such pest control agents can also be filled as compositions in powder form into dispensers in the form of sachets of special paper or of suitable non-woven fabrics (fleeces) and can in that form be introduced into the stored commodities. The pest control agent must then release the hydrogen phosphide formed by hydrolysis through the walls of the sachets to the outside. A further development of this method of application for the fumigation process involves the use of a belt comprising a multitude of pockets for the accommodation of the pest control agent either directly or prepacked in separate sachets.

The problem of the formation of undesired phosphine levels as referred to above, arises for example in the following contexts:

(a) in the manufacture, packaging and storage of phosphine liberating compositions, more particularly those based on hydrolysable metal phosphide such as alkaline earth metal phosphides and earth metal phosphides, e.g. magnesium phosphide, calcium phosphide and aluminium phosphide. When such metal phosphides are processed in order to produce marketable products, notably pest control agents and pest control articles, such as powders or granulates filled into the abovementioned dispensers such as gas and moisture-pervious sachets or composite dispensers composed of a plurality of sachets, e.g. those known as bag blankets, or tablets or pellets, the metal phosphide has to pass through a variety of processing steps such as grinding, mixing with other ingredients, filling into the dispenser sachets or other dispenser articles, pressing into pellets or tablets or other bodies with or without special binding agents, mixing with fibres and bonding agents and shaping the mixture into plates or like bodies which in turn are then covered with moisture-pervious covering material such as paper. As a last step the product is sealed into some gastight and moisture-proof container for storage and transport, wherein the product is kept until just before the intended use. During all of those operations it is in practice difficult, if not impossible, to avoid contact of the metal phosphide with moisture, either environmental humidity or moisture contained in the materials with which the metal phosphide is compounded or laminated or covered and packaged. This results in the unavoidable hydrolysis of some of the metal phosphide and the most undesirable loss of the thereby generated phosphine gas to the manufacturing environment. Regardless of the precautions which may be taken in the factory, it is difficult to avoid completely the escape of some of this phosphine gas into the working environment and the exposure of the workers to the inhalation of highly toxic phosphine gas. Although the concentrations released to the working environment are usually very low indeed and well below the levels permitted by factory control legislation, this state of affairs is nevertheless undesirable. Moreover, the immediate environment of manufacture, i.e. the manufacturing equipment, even though well screened to the working environment, must be vented in some form or another. The concentrations of phosphine gas which are thereby released to the outside of the factory and into the environment are small and will not normally constitute a health or environmental hazard, because the concentrations are so low and because phosphine gas does not cumulate in living organism nor in the environment where it decomposes soon into products which are completely harmless in the low concentrations involved. Nevertheless, even those low concentrations released to the environment create an odour nuisance (a smell, similar to that of garlic or onions and which is also well known to the users of industrial acetylene gas which is normally contaminated with traces of phosphine). No satisfactory solution to this problem has yet been found.

(b) The problem of undesired phosphine release and accumulation continues inside the package. This is due to the unavoidable inclusion of traces of moisture in the package derived from the materials employed. This phosphine accumulation can be dangerous when the package is opened, because the sudden contact of the phosphine with the atmosphere may result in auto-ignition, known as flashing. When the product is in skilled hands, the phenomenon of flashing, is usually harmless, but is nevertheless frightening. However, flashing can be a fire hazard in fire-susceptible environments.

According to the prior art, the aforesaid problems have been counteracted (i) by avoiding as far as possible the inclusion of moisture and contact with moisture in the environment wherein processing and packaging takes place, and the choice of materials such as additive and packaging materials which as far as possible are moisture-free, but can never be moisture-free entirely;

(ii) by including inside the package a means for destroying phosphine, usually in the form of sachets filled with a phosphine destroying composition, including copper oxide and similar heavy metal compositions. This, however, is unsatisfactory, because the phosphine destroying composition is progressively used up, moreover the destruction of phosphine involves moisture-liberating reactions, whereby more moisture becomes available which in turn enters into reaction with the metal phosphide, to release more phosphine. In addition, the use of heavy metal composition is nowadays considered environmentally undesirable.

(c) Finally and very importantly, there is the problem of premature release of phosphine and the buildup of undesirable levels after the metal phosphide composition is removed from the package for actual use, e.g. the distribution of the product in a bulk material or in a storage or transportation space to be fumigated with phosphine. As aforementioned, phosphine gas is extremely toxic, and the exposure of fumigation workers to phosphine gas in appreciable concentrations must be avoided. This can in certain circumstances be very difficult, because of the time delay between the opening of the first package and the introduction of the product into the environment to be fumigated. In the past such operations have sometimes been impossible to carry out without the use of gas masks which are unpleasant to the user and can become defective after prolonged use. Fortunately, in contrast to the use of other gases, it is usually not necessary to wear gas-masks when employing hydrogen phosphide developing pest control agents. Nevertheless, measurable hydrogen phosphide concentrations do arise even during the application stage—in particular when the temperatures and moisture are relatively high.

In the light of ever-increasing environmental consciousness, this fact is giving rise to increasing criticism, because hydrogen phosphide is highly toxic also for humans and higher animals. The fact that the phosphine concentrations in the aforesaid situations, if proper precautions are taken, are well below accepted danger levels is no longer accepted by the public.

The result has been that in some countries or in part of such countries labour organisations are prohibiting the application of hydrogen phosphide developing pest control agents by their members, not the least because, in the past several accidents with fatal consequences had to be contended with, due to faulty user practices.

In order to mitigate the high moisture sensitivity of the abovementioned preparations during handling, packaging and application, attempts had previously been made (DE-GM 1829597) to coat the phosphide particles or the entire tablets with hard paraffin, natural or synthetic resins, waxes or silicones. From those unsuccessful attempts a further proposal arose (U.S. Pat. No. 3,132,067) to completely envelop the individual phosphide particles with a coating, in particular of hard paraffin wax. In order to permit the required access to the phoshide particles of ambient moisture when using the preparation, it was considered necessary to incorporate a bursting agent such as ammonium carbamate.

These coatings of moisture-impervious material, and including ammonium carbamate, although intended to delay the onset of phosphine generation, did not achieve this in practice. If the mass loss of the tablets due to the loss of carbamate was taken into account it was found that these tablets in fact commenced releasing substantial phosphine within minutes of exposure to humidity and continued doing so for several days, albeit at a reduced rate and with a reduced risk of autoignition.

More recent attempts to improve the techniques of coating tablets in order to produce a controlled delay of the onset of phosphine release are still in an early development stage. These techniques are sophisticated and cannot be applied to many products such as plates, powders and sachets, bag blankets and such like. There thus exists a previously unsatisfied need to overcome or mitigate the aforesaid problems.

OBJECTS OF THE INVENTION

Objects of the invention arising from the aforegoing description of the prior art include a method and means for preventing or delaying the formation of undesired phosphine levels in a space or environment, namely (a) in the packages in which phosphine releasing compositions (in particular those based on hydrolysable metal phosphides) are packaged for storage and transport where the object is particularly to avoid phosphine concentrations involving an autoignition hazard when the package is opened; and/or (b) in an environment to be fumigated or its immediate surroundings, where the object is particularly to protect workers temporarily against exposure to hazardous phosphine levels whilst introducing the compositions into the environment.

A further or alternative object in the aforegoing context is to temporarily bind such phosphine gas, as may be released prematurely, in a reversible manner thereby avoiding or mitigating the loss of valuable phosphine.

According to a further or alternative object phosphine gas is bound reversibly to provide a new pest control product offering one or more of the following advantages: (1) reversibility of the phosphine retention and therefore re-usability of the retention medium; (2) substantially no poisonous residues after the release of phosphine and therefore no waste material or disposal problem; (3) reduced autoignition problems; (4) favourable (relatively constant) phosphine release rates; (5) in contrast to metal phosphides, no volume increase of the composition when phosphine is released (phosphine dispensors employing the invention need not be designed to allow for such volume increase).

GENERAL DESCRIPTION OF THE INVENTION

In accordance with one aspect of the present invention, there is provided a method as set out in the opening paragraph, comprising the feature that a phosphine liberating composition preferably comprising a hydrolysable metal phosphide, substantially devoid of ammonia releasing components is brought into and kept in the immediate vicinity of a zeolite having a pore width from 0.3 nm upwards and having an adsorptive capacity for water vapour, phosphine gas or (preferably) both and optionally is subjected to a subsequent step of releasing phosphine adsorbed by the zeolite to an environment to be subjected to pest control. By "substantially devoid of ammonia releasing components" we mean substances such as ammonium carbamate and ammonium carbonate which even at the ambient temperatures, at which the compositions are stored or used, generate sufficiently high vapour pressures of ammonia so as to compete seriously for adsorption sites of the zeolites. On the other hand, additives generating relatively low ammonia vapour pressures such as ammonium salts of fatty acids, e.g. ammonium stearate, can be tolerated.

Ammonia releasing ingredients, notably ammonium carbamate have been incorporated in conventional phosphine releasing compositions for more than two decades in order to prevent autoignition. However, such additives involve a number of drawbacks. They are not only expensive, but they cannot be manufactured completely moisture-free and therefore result in the incorporation of undesirable moisture. Moreover, the released ammonia has an objectionable odour and can do damage to some products. In accordance with the method as defined above, the presence of ammonia releasing ingredients is to be avoided not only for the reasons just stated, but also because zeolites as used in the method have a high adsorptive capacity for ammonia which then competes for adsorption sites against water vapour and phosphine gas. Zeolites used in accordance with the invention have a water content as low as possible, preferably 0.5% $H_2O$ or less, although water contents of up to 1.5% $H_2O$ can still yield good results. Zeolites having a pore width of 0.3 nm or more are effective to adsorb moisture and thereby prevent or delay the access of such moisture to the metal phosphide. This in turn prevents or delays the onset of hydrolysis and release of phosphine gas. A further effect of the zeolite is the adsorption of phoshine once it is formed and present in the environment which contains the zeolite. For this latter effect to take place, zeolites having a pore width of from 0.4 nm, preferably from 0.5 nm upwards are particularly effective. The adsorption of phosphine takes place without moisture liberating reactions, and accordingly, the vicious cycle experienced with prior art phosphine-destroying compositions is not experienced.

Zeolites particularly preferred are those with a pore width in the range from 0.3 to 1.5 nm.

In addition to $PH_3$ adsorption, which is reversible, particularly if the temperature of the zeolite is raised after the adsorption, further phosphine may also be removed irreversibly to a greater or lesser extent by absorption. This involves an irreversible conversion of phosphine into oxidation products. This absorption is particularly effective at relatively high temperatures and results in the effective irreversible removal of phosphine in high temperature conditions of storage where the risk of autoignition is particularly acute. This last-mentioned effect obtained in accordance with the invention is based on phenomena which had not been known previously.

Zeolites suitable for the invention are well known, suitable commercial types being for example known as the so-called 3A, K-Na form, 4A, Na-form, 5A types in the Ca-Na form and 13X-zeolite in the Na-form. The commercial product is normally available in the form of spherical granulate particles of 0.8 to 6 mm diameter or in the form of powder, particle size 2-25 $\mu$m. For the purposes of the present invention it is preferred for these granules not larger than 5 mm, e.g. to be comminuted and to be reduced to a particle size range of 0.001 to 2.5 mm, preferably 0.1 to 2 mm.

The method set out above can be employed in a variety of manners to overcome or mitigate the prior art problems described further above. The method can be applied in the context of packaging and storage of metal phosphide compositions in that the zeolite is included in the package with the metal phosphide. For this purpose the zeolite can be included as a separate item, e.g. as a tablet, pellet or sachet containing the zeolite, separately from the metal phosphide.

However, the zeolite may also be incorporated in the composition itself or as a physical part thereof. Embodiments wherein the zeolite is incorporated in the metal phosphide composition as such, also lend themselves to mitigating or overcoming the aforesaid problems arising during the manufacture of such compositions and products. By admixing the zeolite to the metal phosphide at the earliest possible manufacturing stage, moisture which would otherwise enter into reaction with the metal phosphide is selectively adsorbed by the zeolite and thereby prevented from reacting with the metal phosphide.

The zeolite may alternatively or in addition be applied as a coating enveloping the tablet or pellet or like pressed body. Conventional tabletting aids may be used as binders for the zeolite coating, and are preferably water repellent, e.g. water-insoluble metal soaps, such as magnesium stearate or aluminium stearate, e.g. applied in concentrations of 5 to 30%, preferably 8-20%, e.g. 15% by mass of the coating.

Thus the invention also provides a process for the manufacture of pressed bodies having a zeolite coating wherein into the preferably cylindrical die cavity of a tabletting press, e.g. an excentre press, part of the zeolite forming the coating, e.g. 55 to 85% thereof is introduced in powder form, optionally mixed with a tabletting aid, and pressed into a dish-shaped body, more particularly with the use of an upper die member having a suitable, e.g. frustro-conical taper, this being followed by the introduction of the tablet mixture of metal phosphide with conventional tabletting aids and additives (but substantially devoid of ammonia releasing components as explained further above) followed by the introduction of the balance of the zeolite powder of fine granulate (e.g. 15 to 45% of the total), to complete the filling of the die cavity, preferably levelling the contents of the die cavity, and then pressing the tablet to completion with an appropriately shaped die. The lower die (which serves to eject the completed tablet from the die cavity) and the upper die of the tabletting tool may be flat or have a concave configuration in order to produce tablets having domed ends or being of approximately spherical configuration.

The zeolite may be admixed to the metal phosphide, e.g. in the form of powder mixtures or granules (to be filled into sachets, bag blankets and the like. The mass ratio of metal phosphide to zeolite in a mixture may for example be 1:0.05 to 1:2, depending i.a. on the adsorptive capacity of the zeolite, but is preferably in the range of 1:0.07 to 1:0.3. Such formulations exhibit a delayed release of phosphine, when exposed to air. For example in sachets or in tablets ratios as low as 1:0.1, preferably 1:0.2 were found to be effective. In socalled plates a ratio as low as 1:0.07 is preferred.

The invention may thus be applied to achieving a delayed release of phosphine gas from the phosphine-releasing composition after the opening of the package, more particularly as part of a fumigating method. In that case the delay is effected by virtue of the zeolite inhibiting the access of moisture to the metal phosphide composition, thereby preventing such moisture from entering into reaction with the metal phosphide, and if, in spite of that, some reaction between metal phosphide and moisture takes place to release phosphine gas, the phosphine gas is inhibited or prevented from entering into the environment by being adsorbed or absorbed by the zeolite.

The substantial omission of ammonia releasing ingredients from the products, may make it desirable to apply a variety of various known alternative measures which inhibit autoignition, e.g. operating in the presence of carbon dioxide. In some products no further additives are employed whatsoever.

It may be desirable in a manner known per se to impregnate (in order to hydrophobise) the metal phosphide particles with water repellent substances, e.g. paraffin, stearine, water-insoluble metal soap such as aluminium stearate, magnesium stearate or calcium stearate or zinc stearate. In the case of solid paraffin or stearin impregnation the amount thereof may for example be 1 to 5%, preferably 2 to 4%, in particular 3% by mass. The aforesaid metal soaps may be mixed thoroughly in fine powder form in amounts of 1 to 15%, preferably 3 to 10% by mass.

Also very effective is the hydrophobising of the metal phosphide particles with water repellent organosilicon compounds such as silicones, silanes or siloxanes. Particularly preferred is the use of reactive silanes or siloxanes in accordance with RSA Patent No. 77/7233 (U.S. Pat. Nos. 4,600,584 and 4,421,742).

One effect of the zeolites in the method according to the invention is that they also absorb and decompose diphosphane which tends to autoignite. The invention is therefore usefully applied to compositions having a tendency to form diphosphane, e.g. compositions based on calcium phosphide.

According to a further aspect of the invention, there is provided a gas-tight package for a phosphine liberating composition substantially devoid of ammonia releasing components as hereinbefore explained, said package containing means adapted to inhibit the build-up of phosphine concentrations, comprising the feature that the means comprise a zeolite having a pore width from 0.3 nm upwards and having an adsorptive capacity for water vapour, phosphine gas or both.

The various features described further above in the context of the method can be applied mutatis mutandis to the package in accordance with the invention. This applies to the characteristics of the zeolite. It also applies to the feature that the zeolite may be incorporated in the package as a separate item, e.g. tablet, pellet or sachet containing the zeolite, loosely included in the package or enclosed in a special compartment thereof, which however, must be in communication with the remainder of the package. Alternatively, as in the case of the method, the zeolite may be incorporated in or form part of the phosphine releasing composition.

Defined in a different manner, the present invention also provides a means for preventing or delaying the formation of undesired phosphine levels in a space or environment, the phosphine being derived from phosphine liberating compositions as aforesaid, comprising the feature that the means is a gas pervious container or body containing a zeolite having a pore width from 0.3 nm upwards and having an adsorptive capacity for water vapour, phosphine gas or both. Once again the various aforedescribed features and expedients applicable to the method and to the package also apply mutatis mutandis to the means just defined. The means may for example be a single or multiple gas pervious sachet, e.g. of gas pervious and moisture pervious paper or of gas pervious and moisture pervious fabric or preferably non-woven plastics fibre material (sometimes referred to as a fleece) or the means may be in the form of a pressed body such as a pellet or tablet containing the zeolite, which however, must be sufficiently porous for the purposes of the present invention.

According to a further aspect of the invention, there is provided a phosphine releasing pest control preparation comprising a hydrolysable metal phosphide, more particularly as described above and a means for preventing or delaying the formation of undesired phosphine levels in a space or environment derived from the metal phosphide which preparation contains or is closely associated with a zeolite having a pore width from 0.3 nm upwards and having an adsorptive capacity for water vapour, phosphine gas or both. Once again, the preferred features of the zeolite applicable to the method also apply to the present preparation. The zeolite may be mixed with the metal phosphide and optionally present auxiliary substances. The preparation may be provided in the form of socalled magnesium phosphide plates, i.e. magnesium phosphide-based products wherein the magnesium phosphide is incorporated in a matrix of resinous binder optionally together with a fibrous material, covered with a gas and moisture pervious layer of paper laminated onto the magnesium phosphide-containing core.

The preparation may also be provided in the form of a powder or small granules filled into sachets or bag blankets as described further above.

The zeolite may also be incorporated in a metal phosphide containing mixture pressed into tablets or pellets.

In addition or in the alternative, pressed bodies such as tablets or pellets containing the metal phosphide may be coated with the zeolite.

The finished products according to the invention are packed and stored in gastight containers in an otherwise known manner.

The zeolite in the various embodiments of the invention may be partly loaded with an ignition retarding protective gas, e.g. $CO_2$, $N_2$ or Ar.

It will be appreciated that in the majority of embodiments disclosed above, due to the reversibility of the phosphine adsorption on the zeolite, the zeolite itself, after having adsorbed phosphine as part of its protective function, may subsequently act as a pest control agent. This happens when subsequently, during exposure to the atmosphere, the zeolite once again releases the adsorbed phosphine. Accordingly, a modification of the invention relates to a pest control agent comprising a substance which releases phosphine gas to an environment in which pests are to be controlled and to a process for manufacturing such pest control agent, wherein the substance which releases phosphine gas is a zeolite loaded with reversibly adsorbed phosphine, optionally including additives.

The zeolite may for example be in powder or granule form, preferably in the form of spherical granules of e.g. 1 to 5 mm diameter, preferably 1.5 to 3 mm diameter.

It was found that with certain very active zeolites there can arise a risk of autoignition, particularly if the zeolite is in the form of relatively small particles, if the zeolite is loaded with phosphine to its full capacity. Accordingly it is preferred for the zeolite to be loaded to not more than 66%, preferably not more than 50% of its maximum adsorptive capacity for phosphine gas, in particular with from 20 to 50% such adsorptive capacity.

Optional additives may include autoignition inhibitors known per se in the context of phosphine (other than ammonia-releasing compounds), pressing aids (if the composition is to be tabletted), or binders.

In an alternative embodiment which also avoids the problem of autoignition, the zeolite is partly loaded with carbon dioxide and partly with phosphine gas, e.g. in a ratio of from 2:3 to 4:1, preferably from 1:1 to 2:1. Carbon dioxide when released from the zeolite together with the phosphine, enhances the toxic effect of phosphine gas on pests, e.g. insect pests, in a synergistic manner, apart from the reduced risk of autoignition.

The zeolite should preferably have a pore size of 0.5 nm or more, in particular in the range of 0.5 to 1.0 nm. The zeolite is preferably of a so-called 5A type preferably in the Ca-Na form. The zeolite should be relatively dry and preferably has a moisture content of 1.5% water or less, more preferably 0.5% water or less.

As in the manner known from metal phosphide compositions the pest control agent in accordance with the present invention may also be contained in gas pervious dispenser means which are preferably retrievable, e.g. in sachets made of gas-pervious paper or plastic fabric or non-woven fabrics (also known as fleece) or in cartridges. If in the form of relatively coarse granules, the pore size of the material for the dispenser means may be much coarser than in the case of metal phosphide compositions where a dust problem arises if the pore size is not sufficiently fine.

For purposes of transport and storage, the pest control agent in accordance with the invention are packed in a gas-tight container (e.g. as known in the context of metal phosphide compositions), suitable are for example metal containers, e.g. gas-tight drums or tins or bags or envelopes of metal foil, e.g. aluminum foil or metal foil laminated with one or more layers of plastic film. Also suitable are certain synthetic resin laminates conventionally used in the gas and moisture-proof packaging of metal phosphide compositions, e.g. multiple layer laminates of poly-ethylene and more gas-impervious resins such as polyvinylidene chloride (PVDC). Also suitable are tightly stoppered metal bottles.

According to a further aspect the invention provides a pest control method using phosphine gas, wherein the phosphine is released from a zeolite containing reversibly adsorbed phosphine gas. The phosphine is released from the zeolite on contact with other gases such as nitrogen or oxygen of air. This involves endothermal diffusion phenomena. However, particularly effectively the phosphine is released by being replaced by water molecules of humid air, because the affinity of the zeolite for water is greater than for phosphine gas. This phenomenon is exothermal. Accordingly it is preferred for the zeolite to be exposed to the environment in the presence of humidity. The preferred characteristics of the zeolite are those as set out further above in the description of the pest control agent. In a particular embodiment of the method the zeolite (e.g. contained in special dispenser cartridges) is exposed to a circulatory gas, e.g. a circulatory air stream passing through the environment to be fumigated, e.g. circulated through a bulk commodity such as grain.

For example the zeolite may be exposed to the gas stream in a generator space outside of the environment where the pests are to be controlled from which generator space the gas is then circulated into the environment.

The phosphine may also be released from such generator space (e.g. in the form of a cartridge) at very low concentration into a slow air stream in accordance with the flow through method as described by R. G. Winks "Flow-through phosphine fumigation—a new technique", Stored Grain Protection Conference, 1983, Section 5.1, and in "The Effect of Phosphine on Resistant Insects", GASCA Seminar on Fumigation Technology in Developing Countries, Tropical Development and Research Institute, Storage Department, Slough, 18-2) March 1986. In that method concentrations as low as 4 ug/l over 6 weeks or 50 ug/l over 12 days were completely effective against the most resistant pest strains.

In principle the pest control compositions comprising zeolite reversibly loaded with phosphine may be employed in manners analogous to the manners in which conventional phosphine releasing compositions are employed. Regarding phosphine concentrations and durations of treatment the same principles apply.

The spent zeolite may be recovered, reactivated and reloaded with phosphine or phosphine and carbon dioxide, the reactivation being for example carried out by drying at an elevated temperature, e.g. in the range 300° to 500° C., preferably about 400° C.

The process for manufacturing a pest control agent as set out further above, comprises subjecting a substantially dry zeolite, preferably having the characteristics described further above, to contact with phosphine gas until up to 70%, preferably between 20 and 66%, more preferably from 20 to 50% of total adsorption sites of the zeolite have been loaded with phosphine. According to a particular embodiment, part of the total adsorption sites are loaded with carbon dioxide gas. This is preferably attained by the zeolite being first exposed to carbon dioxide until saturation in respect of carbon dioxide is achieved and thereafter being exposed to phosphine gas, once again preferably until saturation, this time in respect of phosphine gas, has been achieved, and sealing the loaded zeolite into a gastight container.

In DE-OS 27 46 910 a process is described for the recovery of phosphine and methyl phosphane or mixtures of both from waste gases, wherein zeolites having a pore size from 5 to $15 \times 10^{-8}$ cm are contacted with the waste gas mixture at temperatures between $-20°$ and $+30°$ C. up to saturation, whereafter the zeolites are heated to 180° to 230° C. and the thereby desorbed phosphine and/or methyl phosphane gases are recovered. The method of loading the zeolite there described may be employed for purposes of preparing the pest control agent according to the present invention. However, in contrast to the prior art just described, the zeolite is then sealed into airtight containers for storage and transport and ultimate use as a pest control agent. Moreover, the release of the phosphine gas is carried out at ambient temperature due to the gradual displacement of the phosphine from its adsorption sites by atmospheric humidity and not at highly elevated temperatures as described in the reference. At such elevated temperatures part of the phosphine gas is permanently absorbed in the form of oxidation products, resulting in losses of the desired phosphine gas.

In the following the invention will be further described by way of example, partly with reference to the accompanying drawings.

DETAILED DESCRIPTION OF EMBODIMENTS OF THE INVENTION

EXAMPLE 1

Figure 1:
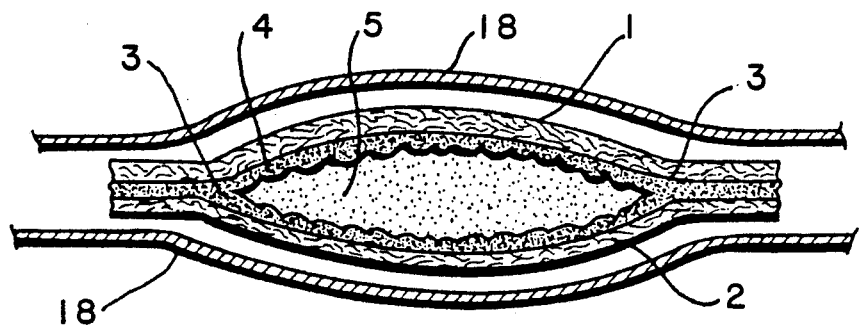
FIG. 1 represents a diagrammatic sectional view of an embodiment of a pest control product, a sachet filled with a pest control agent, according to the invention.

Powderous zeolite X, pore diameter 1.0 nm, Na-form, particle size about 10 μm, moisture content 0.24% $H_2O$ was mixed with technical magnesium phosphide have a particle size of 0.1 to 0.6 mm, homogeneously in a ratio of 9 parts zeolite to 10 parts magnesium phosphide. The composition is filled in the desired amounts into sachets as illustrated in FIG. 1 composed of two layers 1 and 2 of a polyethylene spun bonded non-woven sheet having a mass per unit area of 74.6 g/m². The inside of the sheets 1 and 2 was powder sprinkle coated with a highly porous bonding layer of ethylene vinyl acetate (EVA) having a melting point lower than that of the sheet material to act as a bonding layer in the manner described and claimed in European patent application No. 881083497 and corresponding applications in other countries. The sachet was formed by heat welding the two layers together along their margins to form welding seams 3. The bonding layer is diagrammatically indicated as 4 and the powderous pest control agent content by 5. In practice an optional number of such sachets may be joined together at the welding seams, to form belts composed of an optional number of the sachets in a row. If desired, two or more such rows of sachets may also be united lengthwise side by side. Such composite structures are known in the art as bag blankets. For storage or transport the bag blanket is rolled up and placed in a sheet metal tin, sealed gas-tight. Sachets are similarly packed in gas-tight containers or envelopes similar to those described with reference to FIG. 4.

For testing purposes the sachets had side lengths of 1.4 by 4.2 cm and were each filled with 205 mg of the powder mixture.

For comparison sachets of identical dimensions and characteristics were each filled with 109 mg of the same technical magnesium phosphide but without the zeolite.

The sachets were individually tested for their gas generation characteristics by being exposed to moist air having a relative humidity of 50% at 21° C. in an 11 liter desiccator.

The results are apparent from table 1.

TABLE 1

| Time (min) | Zeolite sachets (ppm $PH_3$) | Comparative sachets (ppm $PH_3$) |
| --- | --- | --- |
| 0 | 0 | 0 |
| 2 | 0 | 7 |
| 5 | 0 | 20 |
| 10 | 0 | 31 |
| 20 | 1 | 68 |
| 30 | 9 | 110 |
| 60 | 50 | 200 |
| 120 | 95 | 350 |

It will be seen that the comparative sachets commenced generating phosphine at a substantial rate almost immediately whilst the sachets according to the invention commenced generating phosphine appreciably only from about 20 minutes onwards, this providing a substantial time delay within which the sachets according to the invention can be handled by fumigating personnel without risk. The time delay is due initially mainly to delaying the access of humidity to the magnesium phosphide, for which purpose pore width of 0.3 nm or more of the zeolite are suitable. A secondary effect is a brief reversible adsorption of phosphine by the zeolite which, however, subsequently is released almost quantitatively, as the zeolite becomes saturated with moisture for this latter effect zeolite having a pore width of 0.5 nm or more are particularly effective.

The sachets can be employed as individual sachets or interlinked by flexible joints in a manner known per se as so-called bag blankets, bag belts or similar composite structures. Instead of magnesium phosphide, aluminium phosphide may be employed. Good effects are achieved with mass ratios of aluminium phosphide to zeolite as low as 1:0.2.

EXAMPLE 2

Figure 2:
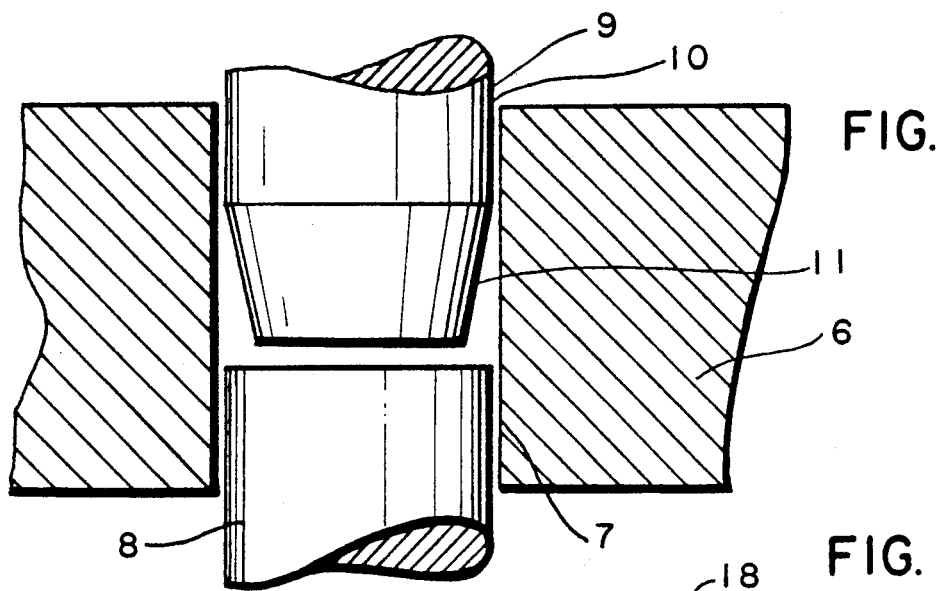
FIG. 2 represents a vertical section of a pressing die for making a coated tablet according to the invention.
Figure 3:
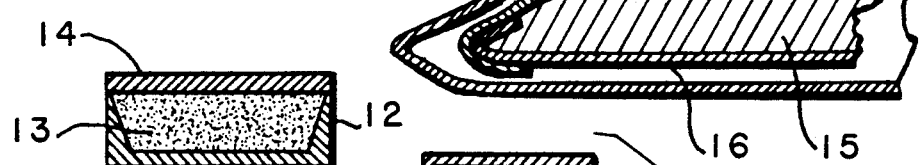
FIG. 3 represents a vertical section through a coated tablet according to the invention, made with a tool according to FIG. 2.

Referring now to FIGS. 2 and 3 of the drawing, a special tabletting tool is used as shown in FIG. 2 comprising a die 6 having a die bore 7, accommodating a lower die 8 having a cylindrical configuration and an upper die ram 9 having an upper cylindrical region 10 followed by a removable lower frusto-conical region 11. In the specific example the bore diameter was 1.9 cm and the bottom diameter of the frustro-conical section 11 was 1.6 cm.

In the first process step 0.5 g of the zeolite powder, 4A type, Na form were placed into the die, followed by vertical downward pressing of the frustro-conical upper die member 10 and 11 to form a dish-shaped zeolite pressing 12 having a rim height of 14 mm. After removing of the frustroconical member 11 and whilst still in the die, 1.55 g technical aluminium phosphide powder, particle size 0.3 to 0.6 mm, impregnated with 3% hard paraffin were introduced through a funnel into the centre of the dish-shaped body 12. Thereafter the dish was filled to completion with zeolite 13X, Na form having a pore diameter of 0.9 nm and a particle size of 0.04 to 0.25 mm and wiped flat on top. The pressing of the tablet was completed by forcing downward the upper die portion 10. This resulted in a firm and stable cylindrical tablet as shown in FIG. 3 having a diameter of 1.9 cm, a height of 0.65 cm and a mass of 2.4 g having a core 13 of aluminium phosphide completely enclosed by the dish-shaped zeolite portion 12 and a zeolite top 14. The zeolite coating had a wall thickness of 0.8 to 1.2 mm.

The tablets were tested in a chamber of 0.035 m³ volume at 21° C. and 40% relative air humidity. The performance was compared against a tablet of the same dimensions containing 70% technical aluminium phosphide, 27% ammonium carbamate and 3% hard paraffin, total mass 3 g, this being a conventional aluminium phosphide tablet composition. The results are apparent from table 2.

TABLE 2

| Time (min) | Zeolite tablet (ppm PH₃) | Comparative tablet (ppm PH₃) |
|---|---|---|
| 0 | 0 | 0 |
| 5 | 0 | 2 |
| 10 | 0 | 5 |
| 15 | 0 | 9 |
| 30 | 0 | 22 |
| 60 | 0.3 | 54 |
| 90 | 1.0 | 90 |

Whereas the prior art tablets commenced generating appreciable amounts of phosphine almost immediately, the phosphine release of the tablet in accordance with the invention commenced after about one hour and was still very slow after 1½ hours.

The tests were repeated at 95% relative air humidity at 20° C. in the same 0.035 m³ chamber. The results are shown in Table 3.

TABLE 3

| Time (min) | Zeolite tablet (ppm PH₃) | Comparative tablet (ppm pH₃) |
|---|---|---|
| 0 | 0 | 0 |
| 5 | 0 | 14 |
| 10 | 0 | 65 |
| 15 | 0.1 | 96 |
| 30 | 3 | 170 |
| 60 | 41 | 390 |
| 90 | 150 | 520 |

The tablets according to the invention were stored in gastight aluminium flasks. Even after 3 months storage no free phosphine gas was detectable in the gas space above the tablets.

Again it is seen that the phosphine release from the tablets according to the invention is delayed substantially, whilst after the time delay the gas release proceeds at a substantially normal rate.

In commerical use the tablets may alternatively be sealed in gastight tubes as described with reference to FIG. 5 (Example 7) of which several may in turn be sealed inside a gastight sheet metal can.

EXAMPLE 3

Magnesium phosphide tablets were prepared by the same procedure as in Example 2, but using instead of the pure zeolite a mixture of 85 parts 4A type, Na-form, particle size 2–10 μm and 15 parts aluminium stearate for forming the dish-shaped portion. 1.5 g paraffin impregnated technical magnesium phosphide (3% paraffin) were filled into the dish, the zeolite top was formed from a mixture of 13X zeolite, Na-form, particle size 30–250 μm and aluminium stearate in the ratio of 90:10. The pressed bodies so formed showed gas generation characteristics at 20° C. at 95% respectively 60% relative humidity in an 0.035 m³ chamber as per Table 4.

TABLE 4

| Time (min) | 95% rel. hum. (ppm PH₃) | 60% rel. hum. (ppm PH₃) |
|---|---|---|
| 0 | 0 | 0 |
| 5 | 0 | 0 |
| 10 | 0 | 0 |
| 15 | 1.2 | 0 |
| 30 | 23 | 0.3 |

TABLE 4-continued

| Time (min) | 95% rel. hum. (ppm PH₃) | 60% rel. hum. (ppm PH₃) |
|---|---|---|
| 60 | 220 | 20 |
| 90 | 420 | 150 |

EXAMPLE 4

Figure 4:
FIG. 4 represents a diagrammatic vertical section through a further embodiment of a pest control product, a so-called "plate", according to the invention.

Magnesium phosphide plates similar to the well known commercial product were prepared as illustrated diagrammatically in FIG. 4.

650 g technical magnesium phosphide of particle size 0.05 to 0.5 mm were mixed homogeneously with an electrical agitator with 300 g polyethylene powder, melting point 130°–140° C., particle size 0.12 to 0.3 mm and, according to the invention, with 50 g zeolite, type 13X, Na-form of particle size 0.2 to 1.5 mm. 100 gramme batches of the powder mixture were each placed on a sheet of filter paper having a moisture content of 1.0 to 2.2% (as determined by 2 hours drying at 105° C.). The filter paper sheet had side lengths of 20×30 cm and a mass per unit of surface area of 105 g/m². By means of a rectangular frame the powder layer was confined uniformly to an area 18 by 28 cm. The layer was heated with infrared radiation to 150° to 160° C. whereafter a filter paper cover sheet of the same size as the first sheet was placed on top, followed by compression of the sample with a heated roller and a pressure of 40 N/cm². The projecting paper margins were folded over and adhesively bonded together using a melting adhesive. The fumigation plate so formed had a thickness of 2.5 mm and was heat-welded into a close fitting envelope of polyethylene-aluminium laminated foil. The product is diagrammatically illustrated in FIG. 4, wherein the plate interior is indicated by 15, the upper and lower sheets of filter paper as 16 and 17 and the gastight envelope as 18.

The product was stored at 15° to 20° C. and at 60° C. respectively and results were compared with a similar prior art sample containing no zeolite.

After 21 days storage at 15° to 20° C. the phosphine content in the gas phase in the envelope of the zeolite sample was 32 ppm and that of the prior art sample 170 000 ppm.

Storage for 21 days at 60° C. yielded the following results:

PH₃ concentration in the gas phase in the envelope of the sample according to the invention 2.9 ppm and in the prior art sample 223 450 ppm.

The particularly low concentration in the 60° C. test was quite unexpected and resulted from the not previously known phenomenon of irreversible PH₃ absorption on zeolites which is more pronounced at relatively high temperatures. The resulting loss in phosphine, amounting to about 0.1 to 0.2% is generally to be considered negligible.

It was also not to be expected that the affinity of the zeolites for moisture would be sufficiently pronounced to preferentially capture humidity entrapped in the product in the manufacturing process and prevent its reaction with the metal phosphide.

The gas generation performance of the plates in accordance with the invention had characteristics similar to those of the prior art plates. The phosphine which is bound temporarily by the zeolite by reversible adsorption is subsequently released completely to the air. Storage at 60° C. results in the irreversible absorption of minor amounts of phosphine (about 0.1 to 0.2%).

In practice a mass ratio of $Mg_3P_2$ to zeolite as low as 1:0.07 is quite effective.

EXAMPLE 5

A prior art magnesium phosphide plate without zeolite additives was sealed into the gastight envelope 18 together with 2 g zeolite-3A, K-Na powder, 2–10 μm and 3 g of a 5A, Ca-Na zeolite in spherical particles, particle size 1–4 mm and stored for 66 days at 15° to 20° C. After that period the phosphine gas concentration in the envelope was 450 ppm, which is substantially below the autoignition concentration. The analysis of the water content and phosphine content respectively of the zeolite powder and granules yielded the results shown in Table 5.

TABLE 5

|  | Water content 0 days | Water content 66 days |
| --- | --- | --- |
| 3 A-powder | 0.45% | 4.8% |
| 5 A-granulate | 0.33% | 1.4% |
|  | $PH_3$ adsorbed | $PH_3$ irreversibly absorbed |
| 3 A-powder | 13 mg | 4.6 mg |
| 5 A-granulate | 26 mg | 0 mg |

EXAMPLE 6

Further plate samples were prepared according to the prior art without zeolite, but various amounts of zeolite were loosely introduced into the envelope together with the plate prior to heat welding and tested for water content, content of adsorbed phosphine and content of irreversibly absorbed phosphine after storage with the results shown in Table 6.

TABLE 6

| Storage 21 days at 15–20° C. | | | |
| --- | --- | --- | --- |
| Amount of zeolite 13X, Na-form, pore diameter 0.9 nm employed per plate (g) | 5 | 10 | 20 |
| Spherical granules: 1–4 mm φ | without $CO_2$ | without $CO_2$ | Saturated with carbon dioxide |
| $PH_3$ conc., gas phase (ppm) | 35 | 14 | 5 |
| Mass $PH_3$ adsorbed/total amount of zeolite (mg) | 1.4 | 6.9 | 6.1 |
| Mass $PH_3$ irreversibly absorbed (mg) | 34 | 32 | 27 |
| Water content prior to use (%) | 0.15 | 0.15 | 0.17 |
| Water content after storage (%) | 0.06 | 0.2 | 0.1 |

It will be noted that the water content of the zeolite changed little.

EXAMPLE 7

Phosphine adsorption-absorption tablets were pressed of 6 mm height and 19 mm diameter from 5A zeolite, Ca-Na form, particle size 0.02 to 0.250 mm and 13X zeolite, Na-form of approximately the same particle size in the mass ratio of 35:65.

Figure 5:
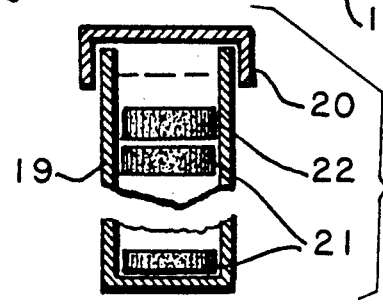
FIG. 5 represents a gastight storage tube containing pest control tablets and a protection tablet according to the invention.

30 aluminium phosphide tablets of conventional dimensions but being free of ammonium carbamate or other ammonia releasing substances are packed into an aluminium tablet tube with the sorption tablet placed on top as illustrated in FIG. 5, wherein the tube is represented by 19 covered gastight by a screwcap 20 and containing metal phosphide tablets 21 of which only two are shown and the sorption tablets according to the invention 22 being on top. The zeolite tablet ensures that the gas phase inside the tube remains substantially phosphine free throughout the period of storage.

EXAMPLE 8

Pellets and round tablets are pressed from 5A and 13X zeolites in a ratio of 1:1. These pressed bodies are admixed to aluminium phosphide and magnesium phosphide containing pellets or round tablets of prior art composition (but free of ammonia) and thus filled into gastight aluminium flasks in a ratio of 1:50. Even after 3 months storage at 50° C., no flashing is observed. The sorption bodies are distributed in use together with the active pressed bodies and at the end of the fumigation period contain no toxic residues, having released by desorption the phosphine absorbed during storage.

EXAMPLE 9

4A, 5A, 13X granulates or granulate mixtures of two or more of these types are admixed to phosphide pressed bodies such as pellets filled in bulk into airtight containers in the same mass ratio as in Example 8, particle size of the zeolite 1–5 mm. The zeolite is scattered together with the pressed bodies when carrying out fumigations.

EXAMPLE 10

40 parts technical aluminium phosphide powder are coated with 3 mass % paraffin and are mixed homogeneously with 57 parts by mass 13X zeolite pore diameter 0.9 nm (particle size 0.005 to 0.200 mm) and pressed into tablets of 2.6 g mass.

When stored in gastight containers no phosphine can be expected in the gas phase. The phosphine generation of the tablets in a 35 liter chamber at 21° C., 50% relative humidity is delayed as shown in Table 7.

TABLE 7

| Time (min) | $PH_3$ (ppm) |
| --- | --- |
| 0 | 0 |
| 5 | 0 |
| 10 | 0 |
| 15 | 0.7 |
| 30 | 3.5 |

EXAMPLE 11

14 parts spherical granules of X-zeolite, Na-form, pore diameter 0.9 nm, granule diameter 1.5–5 mm are homogeneously admixed to a mixture of 10 parts ammonium stearate, 3 parts zinc stearate (particle size of the stearates not more than 30 μm) and 70 parts technical AlP (particle size 0.2 to 0.7 mm) coated with 3 parts hard paraffin.

34 g batches of the mixture are charged into PE-fleece sachets 11×10 cm closed by thermal welding. These were in turn sealed into gastight envelopes of Al-PE laminate foil and stored at 25° C. After 3 months the $PH_3$ concentrations in the gas spaces inside the envelopes were below 1 ppm.

Identical samples were prepared with a preparation having the same composition as above save for the omission of the zeolite. Stored under the same conditions as above the $PH_3$ concentration in the gas phase of the envelopes was 12 500 ppm.

EXAMPLE 12

A zeolite of the 5A type, in the Ca-Na form pore diameter 0.5 nm, having a moisture content of less than 0.5% water is loaded with phosphine gas by phosphine gas being passed through a bed of the zeolite. The zeolite is in the form of a granulate composed of spheres having a diameter of 1–4 mm. The zeolite is fully loaded and contains 9 grammes phosphine per 100 g zeolite. The zeolite is then packed under nitrogen atmosphere into gastight tins for storage.

EXAMPLE 13

The granulate prepared as described in Example 12 is laid in a single layer in a space to be fumigated at 22° C. and 60% relative humidity. After 19 hours the phosphine has been desorbed virtually completely, the residual content of phosphine in the zeolite being now only 0.01%. No residue of absorbed (i.e. oxidised phosphine) could be detected. No autoignition was observed with this relatively coarse granulate.

EXAMPLE 14

For more rapid release of phosphine the zeolite is employed in powder form. In this case exposure to phosphine as described in Example 12 is stopped when the zeolite has been loaded to at the most 50% of its capacity in order to avoid risks of possible autoignition during subsequent use.

EXAMPLE 15

150 g of a 5A zeolite, Ca-Na form, in spherical granule form, 1.5 to 3 mm diameter, bulk density 730 g/dm$^3$ are charged into a glass tube of 3 cm diameter. Carbon dioxide is passed through the bed until saturation has been attained. The saturation limit is detectable by the gradual progression of the zone of heating and the subsequent drop in temperature. 27 g carbon dioxide is adsorbed. Thereafter, pure phosphine gas is passed through the column at a rate of 2.1 ml/sec. After saturation has been attained, the column is briefly rinsed with nitrogen (for 3 minutes). The granulate now contains 5.6% phosphine and 3.4% carbon dioxide. The sample does not autoignite on contact with either air or with liquid water.

The granulate is packed into gastight steel drums.

EXAMPLE 16

The granulate prepared in accordance with Example 15 is exposed in a single layer in an environment to be fumigated at 21° C. and 59% relative humidity. After 20 hours the zeolite contains a mere 0.20% phosphine and 0.3% carbon dioxide. No irreversibly absorbed phosphorus was detectable.

The zeolite was recovered, dried at 400° C. and reloaded as described in Example 15.

The zeolite granulate loaded with adsorbed phosphine can in practice be enclosed in sachets or bag blankets as described with reference to FIG. 1 and stored in gastight containers. Alternatively it is filled into tubular cartridges having inlet and outlet connections at opposite ends. These are packed in gastight cans or drums for storage.

What is claimed is:

1. In a pest control product which comprises a composition which releases phosphine when contacted with atmospheric moisture which is substantially free from an ammonia-releasing component, the improvement wherein the product comprises an amount of a zeolite having pore widths from 0.3 to 1.5 nm and which is effective to delay the initial release of phosphine from the composition when the composition is first contacted with moisture during storage, transport or use.

2. Pest control product as claimed in claim 1, wherein the zeolite has pore widths of at least 0.4 nm.

3. Pest control product as claimed in claim 1 as a gas-tight package in which the zeolite is positioned proximate to but separated physically from and in gas communication with the phosphine-releasing composition.

4. Pest control product as claimed in claim 1, wherein the zeolite is incorporated into the phosphine releasing composition itself or is in direct physical contact therewith.

5. Pest control product as claimed in claim 1, wherein the zeolite is present as a physical mixture with a metal phosphide hydrolyzable by atmospheric moisture, in a mass ratio of the metal phosphide to the zeolite of from 1:0.05 to 1:2.

6. Pest control product as claimed in claim 5, wherein the mixture is in the form of tablets, pellets, sachets, bag blankets or plates.

7. Pest control product as claimed in claim 4, in the form of a pressed body comprising a core of a compressed metal phosphide composition, enveloped in a coating of compressed zeolite alone or combined with one or more additives selected from the group consisting of binders, tabletting agents, water repellant agents and anti-autoignition agents.

8. Pest control product as claimed in claim 4, wherein the zeolite is admixed with a magnesium phosphide composition in which the magnesium phosphide is incorporated as a core in a matrix of resinous binder which optionally contains a fibrous material, which is covered with a gas- and moisture-pervious layer of paper laminated onto the magnesium phosphide-containing core.

9. Pest control product as claimed in claim 5, as a gas-tight package containing the phosphine-liberating composition and the zeolite in gas communication therewith.

10. Pest control product as claimed in claim 1, wherein the zeolite is in the form of a tablet, pellet, or is contained in a sachet.

11. Pest control product as claimed in claim 1, wherein the phosphine-liberating composition is packaged in the gas-tight package is gas communication with the zeolite.

12. Pest control product as claimed in claim 1, wherein the zeolite has a pore size in the range of 0.5 to 1.0 nm and has a moisture content of no more than 0.5% or less.

13. Pest control product as claimed in claim 9, wherein the phosphine-releasing composition is aluminum phosphide or magnesium phosphide.

14. Pest control product which releases phosphine gas to an environment in which pests are to be controlled when the product is exposed to a moisture-containing gaseous atmosphere, wherein the source of the phosphine is a zeolite whose pores are loaded with reversibly adsorbed phosphine.

15. Pest control product as claimed in claim 14, wherein the zeolite has pore widths in the range of from 0.4 to 1.5 nm.

16. Pest control product as claimed in claim 14, wherein the zeolite is in powder or granule form.

17. Pest control product as claimed in claim 14, wherein the zeolite is loaded to not more than 66% of its maximum adsorptive capacity for phosphine gas or is partially loaded with carbon dioxide.

18. Pest control product as claimed in claim 14, wherein the zeolite is contained in a gas pervious dispenser means and packaged for transport and storage in a gas-tight container.

19. Pest control product as claimed in claim 18, wherein the dispenser means is in the form of single or multiple sachets made of gas-pervious paper, plastic fabric or fleece non-woven fabric.

20. In a fumigation method of pest control wherein a pest control product comprising a composition which is substantially free from an ammonia-releasing component and which releases phosphine when the pest control product is exposed to ambient moisture in an environment to be fumigated to thereby release phosphine therefrom, the improvement wherein the pest control product is a product of claim 1.

21. A method according to claim 20, wherein the zeolite has pore widths of from 0.4 to 1.5 nm.

22. A method according to claim 20, wherein the zeolite has a particle size of from 0.001 to 5 mm.

23. A method according to claim 20, wherein the zeolite is a component of the phosphine releasing composition itself or is in physical contact therewith.

24. A method according to claim 20, wherein the zeolite is present as a physical mixture with a metal phosphide hydrolyzable by atmospheric moisture, in a mass ratio of the metal phosphide to the zeolite of from 1:0.05 to 1:2.

25. A method according to claim 24, wherein the dispenser means is in the form of single or multiple sachets made of gas-pervious paper, plastic fabric or fleece non-woven fabric.

26. A method according to claim 14, wherein the zeolite has pore widths of from 0.4 to 1.5 nm; has a particle size range of 0.001 to 5 mm; and wherein the zeolite is present as a physical mixture with a metal phosphide hydrolyzable by atmospheric moisture, in a mass ratio of the metal phosphide to the zeolite of from 1:0.05 to 1:2.

27. A method according to claim 20, wherein the source of the phosphine is a zeolite whose pores are loaded with reversibly adsorbed phosphine.

* * * * *